United States Patent
Gatto, Jr.

(10) Patent No.: US 7,179,478 B2
(45) Date of Patent: Feb. 20, 2007

(54) ANEMONE KILLING MIXTURE AND METHOD FOR AQUARIUMS

(76) Inventor: Joseph C. Gatto, Jr., 25 Elmbrook Dr., Stamford, CT (US) 06906-1110

( * ) Notice: Subject to any disclaimer, the term of this patent is extended or adjusted under 35 U.S.C. 154(b) by 0 days.

(21) Appl. No.: 10/963,701

(22) Filed: Oct. 13, 2004

(65) Prior Publication Data

US 2005/0100576 A1    May 12, 2005

Related U.S. Application Data

(63) Continuation-in-part of application No. 10/623,250, filed on Jul. 18, 2003, now abandoned.

(51) Int. Cl.
*A01N 25/00* (2006.01)
(52) U.S. Cl. ............ 424/405; 424/406; 424/688; 424/693; 119/245; 43/131
(58) Field of Classification Search ............ None
See application file for complete search history.

(56) References Cited

U.S. PATENT DOCUMENTS

| | | |
|---|---|---|
| 3,634,061 A | 1/1972 | Geiger et al. |
| 3,905,797 A | 9/1975 | Kunkel et al. |
| 4,328,638 A | 5/1982 | Smithson |
| 4,505,734 A | 3/1985 | Freedenthal et al. |
| 4,816,163 A | 3/1989 | Lyons et al. |
| 4,857,209 A | 8/1989 | Lyons et al. |
| 4,906,385 A | 3/1990 | Lyons et al. |
| 5,468,739 A | 11/1995 | Whitekettle et al. |
| 5,900,157 A | 5/1999 | Petrille et al. |
| 6,315,910 B2 | 11/2001 | Farmerie et al. |

FOREIGN PATENT DOCUMENTS

EP    0283978    *  9/1988

OTHER PUBLICATIONS

Rhyne et al; Control of Pest Anemone Aiptasia Pallida—Abstract of Marine Ornamentals meeting Nov. 26-Dec. 1, 2001☐☐2002: 58954 Aquasci☐☐DN ASFA1 2002.*

* cited by examiner

*Primary Examiner*—Neil S. Levy
(74) *Attorney, Agent, or Firm*—St. Onge Steward Johnston & Reens LLC

(57) ABSTRACT

A method of killing *Aiptasia* and *Majana anemones* in aquariums comprises filling a dispenser with an anemone killing mixture, comprising purified water, and effective amounts of calcium hydroxide and non-iodized salt, placing a tip of the filled dispenser near a mouth of an anemone and dispensing a small amount of the mixture such that it is consumed by the anemone. An anemone killing mixture comprises effective amounts of calcium hydroxide and non-iodized salt dissolved into and mixed in boiling purified water.

8 Claims, 1 Drawing Sheet

ANEMONE KILLING MIXTURE AND METHOD FOR AQUARIUMS

RELATED APPLICATIONS

This is a continuation in part of U.S. patent application Ser. No. 10/623,250, filed Jul. 18, 2003 now abandoned.

FIELD OF THE INVENTION

The present invention relates to aquarium maintenance and in particular to an anemone killing mixture and method for use in reef aquariums.

BACKGROUND OF THE INVENTION

Anemones are a nuisance and dangerous to corals that hobbyists care for in reef aquariums. *Aiptasia* and *Majana anemones* pack a powerful sting that can irritate or kill desirable corals and clams in the tank. *Aiptasia* are small light brown anemones of the species *A. pallida* and *A. pulchella*. The anemones are typically less than 1.5" long and frequently much smaller. *Aiptasia* are photosynthetic, but will eat things that are small enough for them to catch. The stalk is attached to a hard substrate, usually in a crevice, which allows the anemone to quickly withdraw into the hole when danger approaches. *Aiptasia* reproduce quickly through the process known as pedal laceration which occurs when baby anemones develop from small bits of tissue left behind as the anemone wanders around. *Aiptasia* have remarkable powers of regeneration so cutting, grinding or smashing of the anemones may serve more to propagate the animals that to kill them.

Prior art patents disclose methods for the extermination of algae and macroinverabrates. The term "macroinvertebrates" is defined to include but is not limited to mollusks such as clams, mussels, oysters, and snails; crustaceans such as barnacles; sponges, hydrozoans; sea anemones; bryozoans annelids; and tunicates. None of the prior art patents list direct application of a mixture for elimination of individual unwanted anemones.

U.S. Pat. No. 6,315,910, issued 13 Nov. 2001 to Farmerie, provides a method for controlling snails in aqueous systems which involves treating aqueous systems which contain snails or which are prone to snail infestation with an effective amount of a water-soluble dialkyl diallyl quaternary ammonium polymer (polyquat).

U.S. Pat. No. 5,900,157, issued 4 May 1999 to Petrille, discloses methods for controlling the fouling potential of macroinvertebrates. An effective controlling amount of a polymer that comprises a tannin and a cationic monomer is added to an aqueous system suffering from the fouling potential of macroinvertebrates. The term "macroinvertebrates" is defined to include but is not limited to mollusks such as clams, mussels, oysters, and snails; crustaceans such as barnacles; sponges, hydrozoans; sea anemones; bryozoans; armelids; and tunicates.

U.S. Pat. No. 4,857,209, issued 15 Aug. 1989 to Lyons, claims a method of controlling the fouling potential of macroinvertebrates, such as mollusks, in aqueous systems which comprises adding to the system an effective controlling amount of a water-soluble quaternary ammonium salt.

U.S. Pat. No. 4,816,163, issued 28 Mar. 1989 to Lyons, describes a method of controlling the fouling potential of macroinvertebrates, such as mollusks, in aqueous systems which comprises adding to the system an effective controlling amount of a water-soluble alkyl guanidine salt wherein the alkyl group has from about 8 to about 18 carbons.

U.S. Pat. No. 4,906,385, issued 6 Mar. 1990 to Lyons, discloses a method of controlling the fouling potential of macroinvertebrates, such as mollusks, in aqueous systems. The method comprises adding to the system an effective controlling amount of a water-soluble alkyl guanidine salt wherein the alkyl group has from about 8 to about 18 carbons.

U.S. Pat. No. 5,468,739, issued 21 Nov. 1995 to Whitekettle, indicates methods for controlling the fouling potential of Asiatic clams in aqueous systems are. The methods comprise adding to the aqueous system an effective controlling amount of a tetraalkyl phosphonium salt compound. The preferred compound is tri-butyltetradecyl phosphonium chloride.

U.S. Pat. No. 4,328,638, issued 11 May 1982 to Smithson, puts forth a method of eliminating mussels and the like from an underwater bed. Mussels and related bottom dwelling creatures may be eliminated from an underwater bed by applying to the zone of at least the bottom 2 feet of water above the bed water-soluble sulfite salt such as sodium metabisulfite to substantially deplete dissolved oxygen in the zone. Thereafter, hydrogen sulfide may be directly added to the zone, being stabilized by the absence of oxygen therein to enhance the mussel kill. Thereafter, as fresh water is added to the zone, the hydrogen sulfide and residual sulfites are oxidized to relatively harmless sulfates.

U.S. Pat. No. 4,505,734, issued 19 Mar. 1985 to Freedenthal, concerns basic copper salts such as cupric hydroxide, basic copper chloride, basic copper sulfate and the like with an ailkanolamine result in an unexpectedly beneficial composition useful in a method for treating bodies of water to arrest or eliminate the growth of algae and aquatic weeds.

U.S. Pat. No. 3,634,061, issued 11 Jan. 1972 to Geiger, illustrates the application of a herbicidally effective substantially insoluble copper-containing compound to areas of water infested with undesirable aquatic plants. The compound comes into contact with the plants and is held thereby, destroys said plants with minimal pollution and toxicity to other forms of aquatic life.

U.S. Pat. No. 3,905,797, issued 16 Sep. 1975 to Kunkel, is for an algaecide and herbicide composition for use in controlling the growth of algae and aquatic and terrestrial plants.

What is needed is an anemone killing mixture and method for use in reef aquariums which works instantly and has no adverse affect on the coral or other inhabitants of the aquarium.

DETAILED DESCRIPTION OF THE INVENTION

Figure 1A:
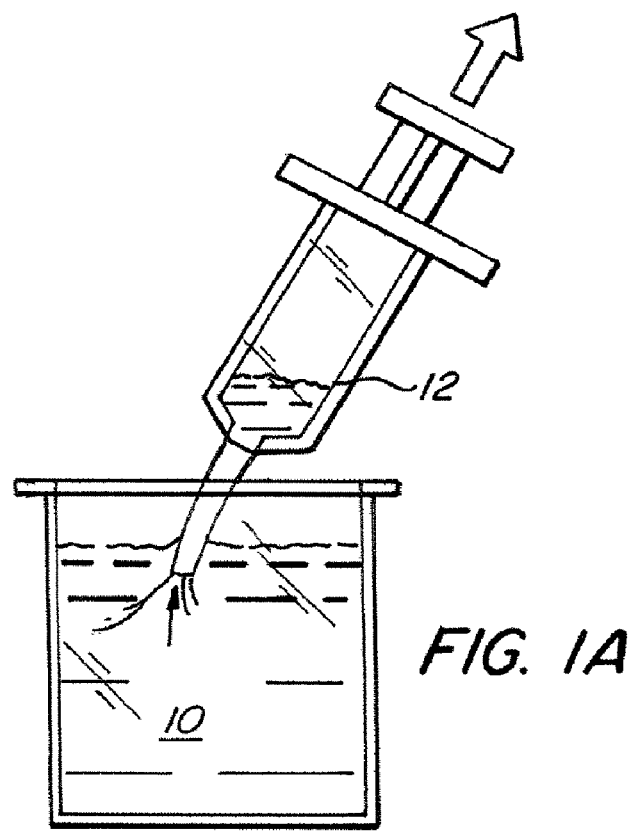
FIG. 1A is an illustration of a step of filling a dispenser with an anemone killing mixture of the method of killing anemones in accordance with the invention.

An object of the present invention is to provide an anemone killing mixture and method for use in reef aquariums, which works instantly and has no adverse affect on the coral or other inhabitants of the aquarium.

One more object of the present invention is to provide a simple anemone killing method, which uses a dispenser such as a syringe to apply the mixture directly to an anemone when it is located underwater in a marine aquarium.

In brief, the present mixture is to be fed to *Aiptasia* and *Majano anemones* located in reef aquariums. These anemones are a nuisance and dangerous to corals that hobbyists actual care for in their aquariums. Within a few seconds of contact of this product the problem anemone dies. When properly applied, the product does not injure other marine life commonly found in marine aquariums.

The anemone killing mixture of the present invention comprises an effective amount of a weakly soluble, strongly alkaline compound, which is preferably calcium hydroxide ($CaOH_2$) but could also be sodium hydroxide or another alkaline compound, and an effective amount of non-iodized salt (NaCl or sea salt) mixed with purified water to form a suspension of $CaOH_2$ in a salt solution. Effective amounts of these components in an anemone killing mixture for reef aquariums comprises: about 1.0 parts by volume of purified water; about 0.35–0.70 parts by volume of dry calcium hydroxide; and about 0.1–0.4 parts by volume of dry non-iodized salt.

A mixture is obtained these components by either pre-heating the liquid to a boil, then mixing it together with the dry components, or by mixing the components, then and heating the mixture until boiling.

The non-iodized salt may be non-iodized sodium chloride; however, in the preferred embodiment, it comprises sea salt. A typical composition for sea salt is Magnesium Chloride ($MgCl_2$) (31.0–35.0%, preferably 33.3%), Potassium Chloride (KCl) (20.0–28.0%, preferably 24.3%), Sodium Chloride (NaCl) (3.0–8.0%, preferably 5.5%), Calcium Chloride ($CaCl_2$) (0.1–0.5%, preferably 0.2%), Bromide (Br—) (0.3–0.6%, preferably 0.5%), Sodium sulphates ($Na_2SO_4$) (0.05–0.2%, preferably 0.15%), Insolubles (0 0.3% or less, preferably 0.03%), and Water of Crystallization (32.0–40.0%, preferably 36.4%).

The purified water preferably comprises water obtained by reverse osmosis.

The method of making the anemone killing mixture is as follows:
(1) Mix the calcium hydroxide in the purified water;
(2) Add the salt and continue mixing;
(3) Heat the combined ingredients until the solution comes to a boil.

An alternate method of making the anemone killing mixture is as follows:
(1) Mix the salt with the water; add sufficient additional salt to create a fully saturated salt water solution:
(2) Mix the saturated salt water solution with the calcium hydroxide;
(3) Heat all the ingredients to boiling.

The most preferred method of making the anemone killing mixture is as follows:
(1) Heat the purified water to boiling;
(2) Mix the salt with the water; continue adding salt until a supersaturated salt water solution is obtained:
(3) Mix the heated saturated salt water solution with the calcium hydroxide to form a suspension.

Figure 1B:
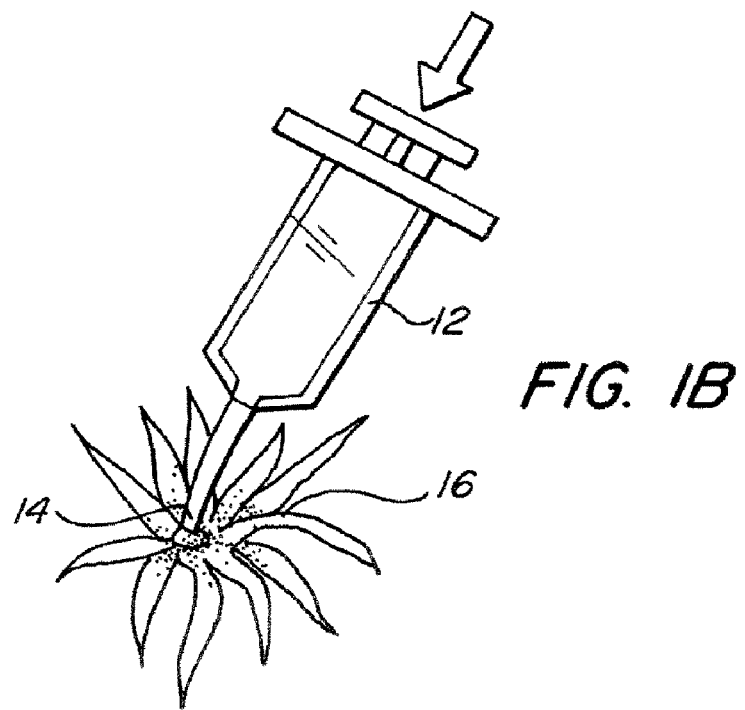
FIG. 1B is an illustration of a step of dispensing an anemone killing mixture to kill an anemone in accordance with the invention.

The method of applying the anemone killing mixture to an anemone is shown in FIGS. 1A and 1B, and comprises steps as follows:
(1) Fill a dispenser 12 (for example a 5 ml syringe) with the anemone killing mixture 10;
(2) Place the tip 14 of the filled dispenser 12 near the mouth or other digestive intake organ of the anemone 16;
(3) Feed the anemone 16 a small amount (between 0.25 to about 1 ml of the mixture). It will ingest the anemone killing mixture and die.

More specifically, the method of killing anemones using the anemone killing mixture for two different types of anemones comprises steps as follows:

For *Aiptasia:*
(1) Fill a dispenser 12 (for example a 5 ml syringe) with the anemone killing mixture 10;
(2) Place the tip of the filled dispenser 12 near the mouth of the anemone *Aiptasia;*
(3) Feed the Aiptasia anemone a small amount (between 0.25 to about 1 ml of the mixture). It will ingest the anemone killing mixture and die.

For *Majana:*
(1) Fill a dispenser 12 (for example, a 5 ml syringe) with the anemone killing mixture 10;
(2) Place the tip 14 of the filled dispenser near the bubble tips of the *Majana anemone;*
(3) Spread product over the *Majana anemone* (between 0.5 to about 1 ml of the mixture). It will ingest the anemone killing mixture and die.

While the mechanism of the method of killing anemones is not certain, it seems likely that the very high salt content of the mixture triggers an uptake of the mixture into the anemone, whereupon the calcium hydroxide reacts with the anemone tissues to destroy the anemone.

The anemone killing mixture of the present invention is reef safe; it is simple to apply by feeding it to *Aiptasia* and *Majana anemones*. The mixture does not require injection into the anemone. The mixture can be applied with aquarium and/or ambient lights on, and the *Aiptasia* and *Majana anemones* do not retract while being fed. The mixture kills the anemone within minutes, causing it to shrivel and die, and leaves very little visible residue, so that there is no need to siphon the dead anemone out of tank after application of the mixture. The mixture has no substantial effect on the water chemistry of the aquarium.

The dispenser used to feed the mixture to the undesirable anemones preferably has a plastic flow control tip, and may be provided with an angled tip to provide greater flexibility when feeding. The mixture is administered from the center of the mouth (oral disk) of the Aiptasia outward across the mouth until it reaches the base of the tentacles. If the mixture is applied only to the tentacles, the anemone will not fully digest the product and will require a second proper feeding in order to be eliminated. The mixture does not cause breakage of the pest anemone or cause reproduction. In some cases, the user may find new smaller Aiptasia that have been hiding, unseen, under or near the larger anemones. These will be eliminated by further feeding of all visible *Aiptasia* with the mixture.

In experiments with the anemone killing mixture of the invention, pest anemones were carefully marked in a 250 gallon marine aquarium. The mixture was applied as described above. Within 20 minutes the treated *Aiptasia* and *Majana anemones* disappeared. In other testing, all *Aiptasia* and *Majano anemones* found in a 4,000 gallon store marine aquarium. *Aiptasia* and *Majano* located on live rock pieces where corals were attached were fed the anemone killing mixture. *Aiptasia* attached to clams, as well as *aiptasia* attached to desirable decorative anemones were also fed the mixture. Water quality was tested twice a week and remained stable. In general, small *Aiptasia* treated with the mixture vanished completely within an half hour; some of the larger *Aiptasia* required two to three doses to completely destroy them. In further testing, the mixture was used in over 100 retail aquarium stores, with uniformly successful results when the above described methods and procedures were filed.

The anemone killing mixture is easy to apply and it kills the anemone within a few seconds of contact. An advantage of the present invention is that the anemone killing mixture will not harm other inhabitants of the reef aquarium. The mixture and method has been tested and has been found to be effective against anemone without harming a variety of desirable fish, shrimp, crabs, snails, anemones and live coral inhabitants.

What is claimed is:

1. A method of killing anemones comprising:
    filling a dispenser with anemone killing mixture comprising purified water, and effective amounts of a weakly soluble alkaline compound and non-iodized salt;
    placing a tip of the filled dispenser near a mouth or digestive intake organ of an anemone;
    dispensing a small amount of the mixture such that it is consumed by the anemone.

2. A method in accordance with claim 1, wherein said anemone comprises an *Aiptasia anemone* and the filled dispenser is placed near a mouth of the *Aiptasia anemone*.

3. A method in accordance with claim 1, wherein said anemone comprises a *Majana anemone* and the filled dispenser is placed near to a bubble tip of the *Majana anemone*.

4. A method in accordance with claim 1, wherein said anemone comprises a *Majana anemone* and the filled dispenser is placed to spread the mixture over the *Majana anemone*.

5. A method in accordance with claims 1, 2, or 3, wherein said weakly soluble alkaline compound comprises calcium hydroxide.

6. A method in accordance with claims 1, 2, or 3 wherein said anemone killing mixture comprising 1.0 part by volume of purified water, 0.35–0.70 parts by volume of calcium hydroxide, and about 0.1 to 0.4 parts by volume of non-iodized salt.

7. A method in accordance with claim 6 wherein said anemone killing mixture has been heated to boiling.

8. A method in accordance with claim 6 wherein the said purified water comprises reverse osmosis water.

* * * * *